US012797227B2

(12) United States Patent
Terndrup

(10) Patent No.: US 12,797,227 B2
(45) Date of Patent: Nov. 17, 2026

(54) BRACE FOR MANAGEMENT OF AN ANATOMICAL STRUCTURE

(71) Applicant: EXO360 APS, København V (DK)

(72) Inventor: Mads Terndrup, Copenhagen (DK)

(73) Assignee: EXO360 APS, København V (DK)

(*) Notice: Subject to any disclaimer, the term of this patent is extended or adjusted under 35 U.S.C. 154(b) by 0 days.

(21) Appl. No.: 18/836,280

(22) PCT Filed: Feb. 2, 2023

(86) PCT No.: PCT/EP2023/052582
§ 371 (c)(1),
(2) Date: Aug. 6, 2024

(87) PCT Pub. No.: WO2023/152025
PCT Pub. Date: Aug. 17, 2023

(65) Prior Publication Data

US 2025/0161089 A1 May 22, 2025

(30) Foreign Application Priority Data

Feb. 10, 2022 (EP) .................................... 22156131

(51) Int. Cl.
*A61F 5/058* (2006.01)

(52) U.S. Cl.
CPC ........ *A61F 5/05825* (2013.01); *A61F 5/0585* (2013.01); *A61F 5/05866* (2013.01)

(58) Field of Classification Search
CPC ................ A61F 5/05825; A61F 5/0585; A61F 5/05866; A61F 5/05841; A61F 5/30; A61F 5/0102; A61F 5/022; A61F 5/05858
See application file for complete search history.

(56) References Cited

U.S. PATENT DOCUMENTS

2015/0025428 A1 1/2015 Liden et al.
2015/0305914 A1 10/2015 Wu et al.
2018/0264718 A1 9/2018 McCluskey et al.

FOREIGN PATENT DOCUMENTS

GB 2580413 A * 7/2020 ............ A61F 5/0118

* cited by examiner

*Primary Examiner* — Ophelia A Hawthorne
(74) *Attorney, Agent, or Firm* — Dority & Manning, P.A.

(57) ABSTRACT

A brace for management of an anatomical structure and method for manufacturing the brace includes a primary anatomical structure, a secondary anatomical structure, and a joint and/or an injury between the primary anatomical structure and the secondary anatomical structure. The brace includes a first brace part extending from a first primary brace part end to a first secondary brace part end and being adapted for positioning to cover a first part of the anatomical structure extending over the joint and/or injury such that the first primary brace part end is located on the primary anatomical structure and the first secondary brace part end is located on the secondary anatomical structure. The first brace part includes a first outer shell and one or more first lattice structures attached to a first inner side of the first outer shell.

14 Claims, 6 Drawing Sheets a) b)

BRACE FOR MANAGEMENT OF AN ANATOMICAL STRUCTURE

CROSS-REFERENCE TO RELATED APPLICATIONS

This application is a § 371 national stage entry of International Application No. PCT/EP2023/052582, filed Feb. 2, 2023, which claims priority to European Application No. 22156131.9, filed Feb. 10, 2022, the entire contents of which are incorporated herein by reference.

The present disclosure relates generally to orthoses, e.g. externally applied devices moving and/or stabilizing parts of an anatomical structure, such as a limb, across one or more anatomical joint(s) and/or an injury, such as to influence the structural and/or functional characteristics of the neuromuscular and skeletal system. For example, such as to allow immobilisation or stabilisation of an anatomical structure and pain relief and/or management thereof.

BACKGROUND

Anatomical structures include joints and bones, wherein joints connect bones and allow movement in the skeletal system. Injury to anatomical structures might involve bony structures, ligaments, muscle tears, tendon ruptures and more. Most injuries are stable and will heal without or with little compromise to the functional whole across the joint. However, certain injuries are severe and cause instability across the anatomical joint, requiring internal or external fixation (either through surgical stabilization or an external cast/brace) and/or reduction (e.g. in case of dislocation), and may require realignment and/or rehabilitation to restore optimal range of motion across the affected joint.

Conventionally, a plaster cast may be provided to immobilize and/or stabilize the injured limb. However, applying a plaster cast is a time consuming procedure and requires different tools as well as multiple healthcare provides. Furthermore, injured limbs may need multiple attempts of casting, which with a conventional plaster cast means starting over and hoping for a better second result.

Even more, when applying a plaster cast, the anatomical structure might be swollen (e.g. due to the injury). Hence, if applying a plaster cast, the cast may loosen due to reduction in swelling.

SUMMARY

It is an object of the present disclosure to provide improvements of the prior art and/or to solve or reduce problems known from the prior art, such as, for example, the problems mentioned above. More particularly, it is an object of the present disclosure to provide a solution for management of an anatomical structure, which is easy to use, allows quick and precise fitting and/or enhances flexibility and adjustability. Effectively, the disclosed solution may reduce time spent on treatment of injured limbs as well as save costs, freeing up valuable healthcare resources.

Accordingly, a brace and a method for manufacturing the brace are disclosed. The brace is a brace for management of an anatomical structure comprising a primary anatomical structure, a secondary anatomical structure, and a joint and/or an injury between the primary anatomical structure and the secondary anatomical structure. The anatomical structure may be an injured anatomical structure.

The brace comprises a first brace part extending from a first primary brace part end to a first secondary brace part end and being adapted to be positioned to cover a first part of the anatomical structure extending over the joint and/or injury such that the first primary brace part end is located on the primary anatomical structure and the first secondary brace part end is located on the secondary anatomical structure.

The first brace part comprises a first rigid outer shell and one or more first lattice structures attached to a first inner side of the first rigid outer shell. The one or more first lattice structures have a first height in a height direction normal to the first inner side of the first rigid outer shell in a non-compressed state. The first height may be between 3 and 50 mm, such as between 5 and 30 mm, such as between 10 and 20 mm. The one or more first lattice structures are adapted to: in response to increasing compression from the non-compressed state to a first compression amount in the height direction, exhibit stress increasing at a first rate, and in response to increasing compression from the first compression amount to a second compression amount in the height direction, exhibit stress being uniform or increasing at a second rate lower than the first rate.

The first compression amount may correspond to 5% of the first height, such as less than 5% of the first height. The second compression amount may correspond to more than 50% of the first height, such as 50%. 60%, 70%, 80% or 90% of the first height, or more than 60%, 70%, 80% or 90% of the first height. The second rate of stress increase between the first compression amount and the second compression amount may be less than 50%, such as less than 25%, such as less than 10%, such as less than 5%, such as less than 1% of the first rate of stress increase.

The one or more first lattice structures are further adapted to, in response to decreasing compression from the first compression amount and/or the second compression amount to the non-compressed state, return to the first height, e.g. within a predetermined time period. The predetermined time period may be less than 30 minutes, such as less than 10 minutes, such as less than 1 minute, such as less than 30 seconds, such as less than 10 seconds, such as less than 1 second, such as less than 0.5 seconds.

The first compression amount and/or the second compression amount corresponds to a deformation which is reversible and non-permanent. Thus, in response to decreasing compression from the first compression amount and/or from the second compression amount, the one or more lattice structures return to their initial heights, i.e., the first height.

The first compression amount may correspond to a stress, such as applied pressure, between 5-40 mmHg, such as between 10-36 mmHg, such as between 15-20 mmHg. The second compression amount may correspond to a pressure between 5-40 mmHg, such as between 10-36 mmHg, such as between 15-20 mmHg.

The one or more first lattice structures includes a first primary lattice structure covering a first primary region and a first secondary lattice structure covering a first secondary region. The average stress exhibited by the first primary lattice structure in response to compression between the first compression amount and the second compression amount in the first primary region is lower than the average stress exhibited by the first secondary lattice structure in response to compression between the first compression amount and the second compression amount in the first secondary region.

As mentioned, a method for manufacturing a brace for management of the anatomical structure, such as the brace as disclosed above, is also disclosed.

The method comprises providing a first rigid outer shell for a first brace part of the brace extending from a first primary brace part end to a first secondary brace part end, wherein the first brace part is adapted to be positioned to cover a first part of the anatomical structure extending over the joint and/or injury such that the first primary brace part end is located on the primary anatomical structure and the first secondary brace part end is located on the secondary anatomical structure.

The method further comprises forming one or more first lattice structures having a first height in a height direction in a non-compressed state. The one or more first lattice structures are adapted to: in response to increasing compression from the non-compressed state to a first compression amount in the height direction, exhibit stress increasing at a first rate, and in response to increasing compression from the first compression amount to a second compression amount in the height direction, exhibit stress being uniform or increasing at a second rate lower than the first rate.

The first compression amount may correspond to 5% of the first height, such as less than 5% of the first height. The second compression amount may correspond to more than 50% of the first height, such as 50%. 60%, 70%, 80% or 90% of the first height, or more than 60%, 70%, 80% or 90% of the first height. The second rate of stress increase between the first compression amount and the second compression amount may be less than 50%, such as less than 25%, such as less than 10%, such as less than 5%, such as less than 1% of the first rate of stress increase.

The one or more first lattice structures are further adapted to, in response to decreasing compression from the first compression amount and/or the second compression amount to the non-compressed state, return to the first height, e.g. within a predetermined time period. The predetermined time period may be less than 30 minutes, such as less than 10 minutes, such as less than 1 minute, such as less than 30 seconds, such as less than 10 seconds, such as less than 1 second, such as less than 0.5 seconds. The one or more first lattice structures are formed to include a first primary lattice structure covering a first primary region and a first secondary lattice structure covering a first secondary region, wherein the average stress exhibited by the first primary lattice structure in response to compression between the first compression amount and the second compression amount in the first primary region is lower than the average stress exhibited by the first secondary lattice structure in response to compression between the first compression amount and the second compression amount in the first secondary region.

The method further comprises attaching the one or more first lattice structures to a first inner side of the first rigid outer shell, such that the height direction of the one or more first lattice structures are arranged normal to the first inner side of the first rigid outer shell.

The present disclosure provides a solution, which is quick and easy to use, is precise and adjustable, and which can be applied without any extra tools. Furthermore, the present disclosure provides for faster and more standardized manufacturing of a brace for managing an (injured) anatomical structure. It is a further advantage of the present disclosure that a brace may be provided, which reduces patient discomfort while recovering from an injury. The present disclosure further reduces the need for more complex procedures, such as surgical interventions, caused by inefficient immobilization or stabilising of an injured anatomical structure.

The brace may comprise a second brace part extending from a second primary brace part end to a second secondary brace part end. The second brace part may be adapted to be positioned to cover a second part of the anatomical structure. The second part of the anatomical structure may be opposite the first part of the anatomical structure. The second brace part may be adapted to be positioned to cover the second part of the anatomical structure extending over the joint and/or injury such that the second primary brace part end is located on the primary anatomical structure and the second secondary brace part end is located on the secondary anatomical structure. The second brace part may comprise a second rigid outer shell. Accordingly, the method may comprise providing such second rigid outer shell for the second brace part of the brace.

In some examples, the second brace part may be without a lattice structure, i.e. providing a hard shell to be positioned to cover the second part of the anatomical structure. Alternatively, the second brace part may comprise one or more second lattice structures attached to a second inner side of the second rigid outer shell. The one or more second lattice structures may have a second height in a height direction normal to the second inner side of the second rigid outer shell in a non-compressed state. The second height may be between 3 and 50 mm, such as between 5 and 30 mm, such as between 10 and 20 mm. Furthermore, like for the one or more first lattice structures, the one or more second lattice structures may be adapted to: in response to increasing compression from the non-compressed state to a primary compression amount in the height direction, exhibit stress increasing at a primary rate, and in response to increasing compression from the primary compression amount to a secondary compression amount in the height direction, exhibit stress being uniform or increasing at a secondary rate lower than the primary rate.

The primary compression amount may correspond to 5% of the second height, such as less than 5% of the second height. The secondary compression amount may correspond to more than 50% of the second height, such as 50%. 60%, 70%, 80% or 90% of the second height, or more than 60%, 70%, 80% or 90% of the second height. The secondary rate of stress increase between the primary compression amount and the secondary compression amount may be less than 50%, such as less than 25%, such as less than 10%, such as less than 5%, such as less than 1% of the primary rate of stress increase.

The one or more second lattice structures may further be adapted to, in response to decreasing compression from the primary compression amount and/or the secondary compression amount to the non-compressed state, return to the second height, e.g. within a predetermined time period, which may be similar to the predetermined time period as described in relation to the one or more first lattice structures.

The primary compression amount and/or the secondary compression amount corresponds a deformation which is reversible and non-permanent. Thus, in response to decreasing compression from the primary compression amount and/or secondary compression amount, the one or more lattice structures return to their initial heights, i.e. the second height.

The primary compression amount may correspond to a stress, such as applied pressure, between 5-40 mmHg, such as between 10-36 mmHg, such as between 15-20 mmHg. The secondary compression amount may correspond to a pressure between 5-40 mmHg, such as between 10-36 mmHg, such as between 15-20 mmHg.

The one or more second lattice structures may be formed to include a second primary lattice structure covering a second primary region and a second secondary lattice structure covering a second secondary region. The average stress exhibited by the second primary lattice structure in response to compression between the primary compression amount and the secondary compression amount in the second primary region may be lower than the average stress exhibited by the second secondary lattice structure in response to compression between the primary compression amount and the secondary compression amount in the second secondary region.

The first rigid outer shell and/or the second rigid outer shell may be formed to fit the anatomical structure. The first inner side of the first rigid outer shell and/or the second inner side of the second rigid outer shell may be concave, such as to at least partially enclose the respective part of the anatomical structure, i.e. the first part or the second part of the anatomical structure. The first rigid outer shell and/or the second rigid outer shell may, for example, be made of polyurethane or polypropylene.

The brace may be adapted to be positioned on the anatomical structure such that the first primary region and/or the second primary region is positioned on a part of the anatomical structure having a bony prominence. Alternatively or additionally, the brace may be adapted to be positioned on the anatomical structure such that the first secondary region and/or the second secondary region is positioned on a part of the anatomical structure with soft tissue.

The brace may be adapted to be positioned on the anatomical structure such that the first primary region and/or the second primary region is positioned closer to the joint and/or injury of the anatomical structure than the first secondary region and/or the second secondary region. For example, the brace may be adapted to be positioned on the anatomical structure such that the first primary region and/or the second primary region is positioned over the joint and/or over the injury.

The brace may be adapted to be positioned on the anatomical structure such that harder regions, e.g. the first primary region, the second primary region and optionally further regions, are located to provide for a sufficient three-point fixation of the injury of the anatomical structure.

The one or more first lattice structures may include a first tertiary lattice structure. The first tertiary lattice structure may cover a first tertiary region. The average stress exhibited by the first primary lattice structure in response to compression between the first compression amount and the second compression amount in the first primary region may be lower than the average stress exhibited by the first tertiary lattice structure in response to compression between the first compression amount and the second compression amount in the first tertiary region. The average stress exhibited by the first tertiary lattice structure in response to compression between the first compression amount and the second compression amount in the first tertiary region may be between the average stress exhibited by the first primary lattice structure in response to compression between the first compression amount and the second compression amount in the first primary region and the average stress exhibited by the first secondary lattice structure in response to compression between the first compression amount and the second compression amount in the first secondary region.

The one or more second lattice structures may include a second tertiary lattice structure. The second tertiary lattice structure may cover a second tertiary region. The average stress exhibited by the second primary lattice structure in response to compression between the primary compression amount and the secondary compression amount in the second primary region may be lower than the average stress exhibited by the second tertiary lattice structure in response to compression between the primary compression amount and the secondary compression amount in the second tertiary region. The average stress exhibited by the second tertiary lattice structure in response to compression between the primary compression amount and the secondary compression amount in the second tertiary region may be between the average stress exhibited by the second primary lattice structure in response to compression between the primary compression amount and the secondary compression amount in the second primary region and the average stress exhibited by the second secondary lattice structure in response to compression between the primary compression amount and the secondary compression amount in the second secondary region.

The first primary lattice structure and the first secondary lattice structure and optionally the first tertiary lattice structure may be independently manufactured lattice structures. Alternatively or additionally, the second primary lattice structure and the second secondary lattice structure and optionally the second tertiary lattice structure may be independently manufactured lattice structures. The independently manufactured lattice structures may be attached to their respective rigid outer shell to form the one or more lattice structures.

Alternatively, the one or more first lattice structures may be integrally formed. For example, the first primary lattice structure and the first secondary lattice structure and optionally the first tertiary lattice structure may be integrally formed. Alternatively or additionally, the one or more second lattice structures may be integrally formed. For example, the second primary lattice structure and the second secondary lattice structure and optionally the second tertiary lattice structure may be integrally formed. For example, forming the one or more first lattice structures may comprise forming a single first lattice structure comprising the first primary lattice structure and the first secondary lattice structure and optionally the first tertiary lattice structure. The single first lattice structure may be adapted to extend from the first primary brace part end to the first secondary brace part end. Alternatively or additionally, forming the one or more second lattice structures may comprise forming a single second lattice structure comprising the second primary lattice structure and the second secondary lattice structure and optionally the second tertiary lattice structure. The single second lattice structure may be adapted to extend from the second primary brace part end to the second secondary brace part end.

The one or more first lattice structures and/or the one or more second lattice structures may be elastomeric and/or polymeric lattice structures. For example, the one or more first lattice structures and/or the one or more second lattice structures may be made of polyurethane, such as a polyurethane elastomer. The one or more first lattice structures may comprise a plurality of interconnected flexible struts, which may form repeating unit cells. The unit cells may be triangular, quadratic, pentagonal, hexagonal, or other geometric shapes.

The one or more first lattice structures and/or the one or more second lattice structures may be formed by additive manufacturing, such as 3D printing and/or resin printing. For example, the one or more first lattice structures may be formed by selective laser sintering and/or by digital light synthesis (DLS) of Carbon Inc. An exemplary process for forming the one or more first and/or second lattice structures may be found in US 2018/0264718 A1. Accordingly, the one or more first and/or second lattice structures may be in accordance with the lattices of US 2018/0264718 A1.

The lattice structures may differ by their geometrical shape, their thickness of struts, and/or their length of struts. For example, the first primary lattice structure may differ from the first secondary lattice structure, the first primary lattice structure may differ from the first tertiary lattice structure, and/or the first secondary lattice structure may differ from the first tertiary lattice structure, e.g. by their geometrical shape, their thickness of struts, and/or their length of struts. The second primary lattice structure may differ from the second secondary lattice structure, the second primary lattice structure may differ from the second tertiary lattice structure, and/or the second secondary lattice structure may differ from the second tertiary lattice structure, e.g. by their geometrical shape, their thickness of struts, and/or their length of struts. The thickness (e.g. diameter) of struts may be between 0.1 mm and 1 mm. The length of struts may be between 0.5 mm and 10 mm, such as between 1 mm and 5 mm, such as between 1 mm and 2 mm.

Geometrical shape, thickness of struts, and/or length of struts of the first primary lattice structure, the first secondary lattice structure, the first tertiary lattice structure, the second primary lattice structure, the second secondary lattice structure, and/or the second tertiary lattice structure may vary along the height direction.

The brace may comprise one or more fasteners adapted to fasten the brace to the anatomical structure. The one or more fasteners may include one or more straps. The fasteners, such as the straps, may include hook and loop fasteners. The fasteners, such as the straps, may facilitate incrementally tightening or loosening the fastening of the brace to the anatomical structure. The fasteners, such as the straps, may allow for easy opening and re-closure, such as to allow repositioning of the brace. The one or more fasteners, such as the straps, may be adapted to fasten the first brace part to the second brace part, e.g. so as to fasten the brace around the anatomical structure.

The method for manufacturing the brace may comprise obtaining a three-dimensional model of the anatomical structure, e.g. including the location of the joint and/or the injury. Forming the one or more first lattice structures and/or the one or more second lattice structures may be based on the three-dimensional model. The three-dimensional model may include information of tissue type at a plurality of locations of the anatomical structure, such as positions of bony prominences, soft tissue, ligaments, superficial nerves etc. Forming the one or more first lattice structures and/or attaching the one or more first lattice structures to the first inner side of the first rigid outer shell may comprise arranging the first primary region to cover a part of the anatomical structure having one or more bony prominences and/or arranging the first secondary region to cover a part of the anatomical structure having soft tissue. Forming the one or more second lattice structures and/or attaching the one or more second lattice structures to the second inner side of the second rigid outer shell may comprise arranging the second primary region to cover a part of the anatomical structure having one or more bony prominences and/or arranging the second secondary region to cover a part of the anatomical structure having soft tissue.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Figure 1:
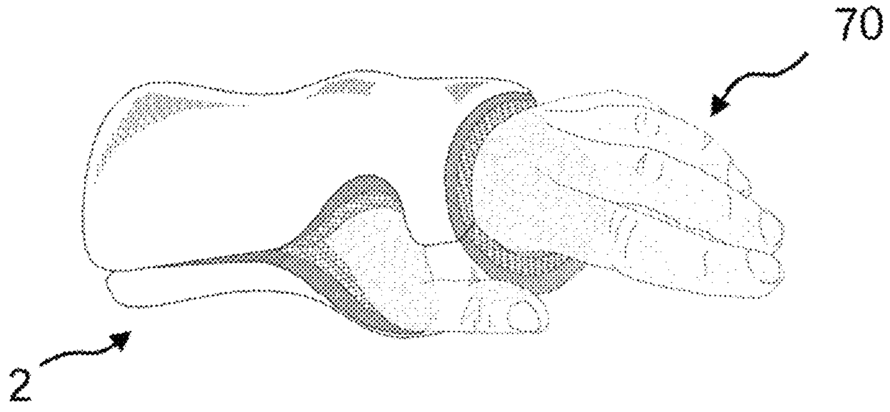
FIG. 1 is a schematic diagram illustrating an exemplary brace.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 is a schematic diagram illustrating an exemplary brace 2 according to the present disclosure. The brace 2 is attached to an anatomical structure 70, in the present case a wrist. The exemplary anatomical structure 70 is further schematically illustrated in FIG. 2. Although in the presently illustrated example, the anatomical structure 70 is a wrist, it should be understood that the brace according to the present disclosure may be shaped to be fitted to other anatomical structures, such as an ankle, a knee, an elbow etc.

The anatomical structure 70 comprises a primary anatomical structure 72, e.g. the forearm, and a secondary anatomical structure 74, e.g. the hand. The anatomical structure 70 further comprises a joint 76, e.g. the wrist and/or an injury 78, e.g. a bone fracture, tissue damage, or similar. The joint 76 and/or the injury 78 is located between the primary anatomical structure 72 and the secondary anatomical structure 74.

Figure 2:
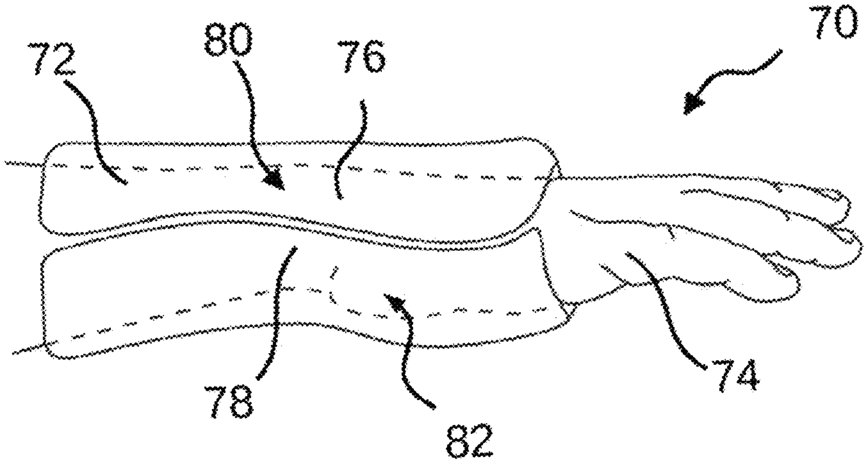
FIG. 2 is a schematic diagram illustrating an exemplary anatomical structure.
Figure 3:
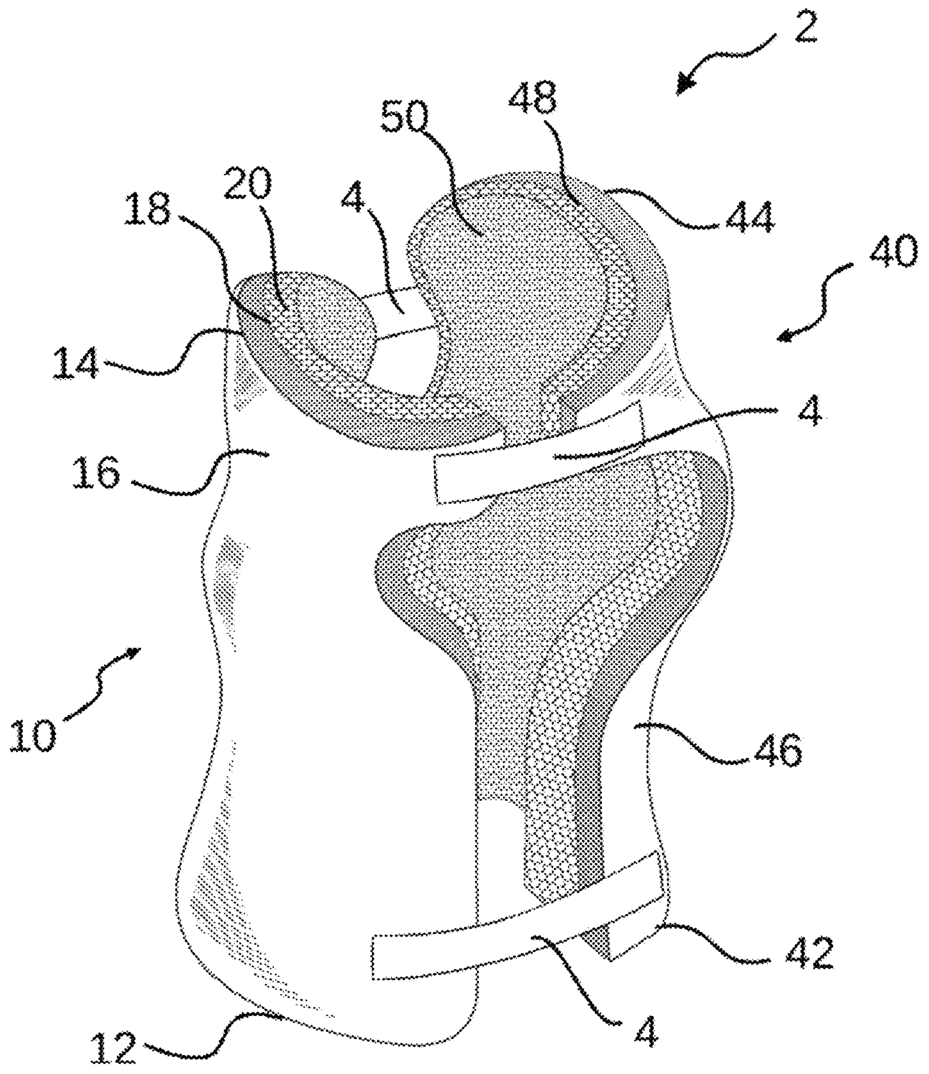
FIG. 3 is a schematic diagram illustrating the exemplary brace.

FIG. 3 is a schematic diagram illustrating the exemplary brace 2. The brace 2 comprises a first brace part 10 extending from a first primary brace part end 12 to a first secondary brace part end 14. The first brace part 10 is adapted to be positioned to cover a first part 80 (see FIG. 2) of the anatomical structure 70 extending over the joint 76 and/or injury 78, such that the first primary brace part end 12 is located on the primary anatomical structure 72 and the first secondary brace part end 14 is located on the secondary anatomical structure 74.

The first brace part 10 comprises a first rigid outer shell 16. The first rigid outer shell 16 is sufficiently rigid to provide the necessary stability of the brace 2 to support the anatomical structure 70. The first rigid outer shell 16 comprises a first inner side 18. The first inner side 18 is concave to at least partially enclose the first part 80 of the anatomical structure 70. The first brace part 10 further comprises one or more first lattice structures 20 attached to the first inner side 18 of the first rigid outer shell 16. The one or more first lattice structures 20 may be elastomeric and/or polymeric lattice structures. In some examples, the one or more first lattice structures 20 may be divided into a plurality of individually manufactured portions each being attached to the first inner side 18. In other examples, the one or more first lattice structures 20 may be formed by a single lattice structure extending from the first primary brace part end 12 to the first secondary brace part end 14. The one or more first lattice structures 20 may be attached to the first inner side 18 by gluing, by hooks and loops, or by another attachment method known in the art. The one or more first lattice structures 20 may be only lightly attached, as the positioning of the brace 2 on the anatomical structure will help maintain the position of the one or more first lattice structures 20 with respect to the first rigid outer shell 16.

The brace 2, as exemplified in FIG. 3, comprises a second brace part 40. The second brace part 40 extends from a second primary brace part end 42 to a second secondary brace part end 44. The second brace part 40 is adapted to be positioned to cover a second part 82 (see FIG. 2) of the anatomical structure 70 extending over the joint 76 and/or injury 78, such that the second primary brace part end 42 is located on the primary anatomical structure 72 and the second secondary brace part end 44 is located on the secondary anatomical structure 74. The second part 82 of the anatomical structure may be opposite the first part 80 of the anatomical structure. For example, the first part 80 may be a posterior side of the forearm, wrist, hand, as illustrated in FIG. 2, and the second part 82 may be an anterior side of the forearm, wrist, hand, as illustrated in FIG. 2.

The second brace part 40 comprises a second rigid outer shell 46. The second rigid outer shell 46 is sufficiently rigid to provide the necessary stability of the brace 2 to support the anatomical structure 70. The second rigid outer shell 46 comprises a second inner side 48. The second inner side 48 is concave to at least partially enclose the second part 82 of the anatomical structure 70. The second brace part 40 further comprises one or more second lattice structures 50 attached to the second inner side 48 of the second rigid outer shell 46. The one or more second lattice structures 50 may be elastomeric and/or polymeric lattice structures. In some examples, the one or more second lattice structures 50 may be divided into a plurality of individually manufactured portions each being attached to the second inner side 48. In other examples, the one or more second lattice structures 50 may be formed by a single lattice structure extending from the second primary brace part end 42 to the second secondary brace part end 44. The one or more second lattice structures 50 may be attached to the second inner side 48 by gluing, by hooks and loops, or by another attachment method known in the art. The one or more second lattice structures 50 may be only lightly attached, as the positioning of the brace 2 on the anatomical structure will help maintain the position of the one or more second lattice structures 50 with respect to the second rigid outer shell 46.

Figure 8:
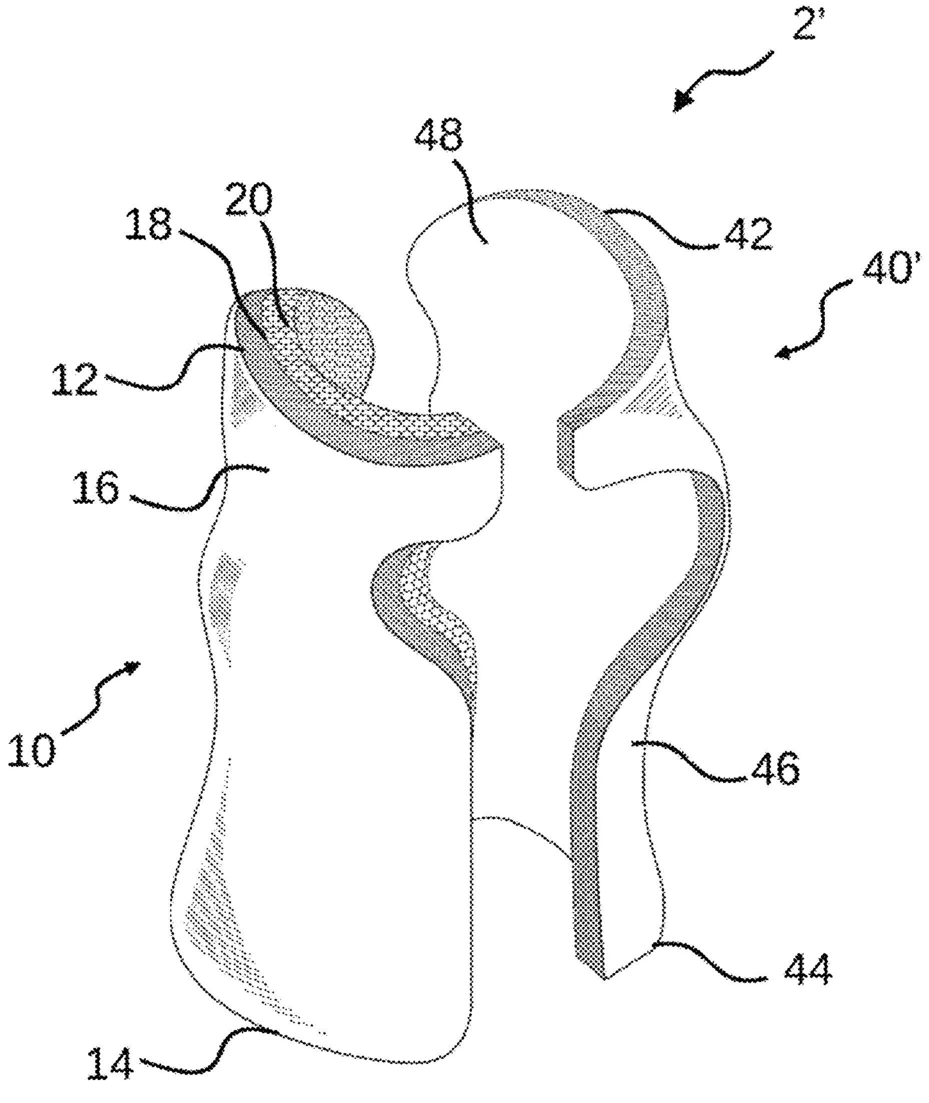
FIG. 8 is a schematic diagram illustrating an exemplary brace.

In some examples, the second brace part 40 may omit the one or more second lattice structures 50 (see FIG. 8). In some other examples, the second brace part 40 may be omitted.

The brace 2 comprises fasteners 4 adapted to fasten the brace 2 to the anatomical structure 70. For example, the fasteners may include straps, such as hook and loop straps. The fasteners 4 may facilitate incrementally tightening or loosening of the brace. The fasteners 4, in the illustrated example, are adapted to fasten the first brace part 10 to the second brace part 40, so as to fasten the brace 2 around the anatomical structure 70. In some examples, e.g. if omitting the second brace part 40, the fasteners 4 may fasten the brace 2 directly to the anatomical structure 70, e.g. by the fasteners extending from one side of the first brace part 10 and around the anatomical structure 70 to the opposite side of the first brace part 10.

Figure 4:
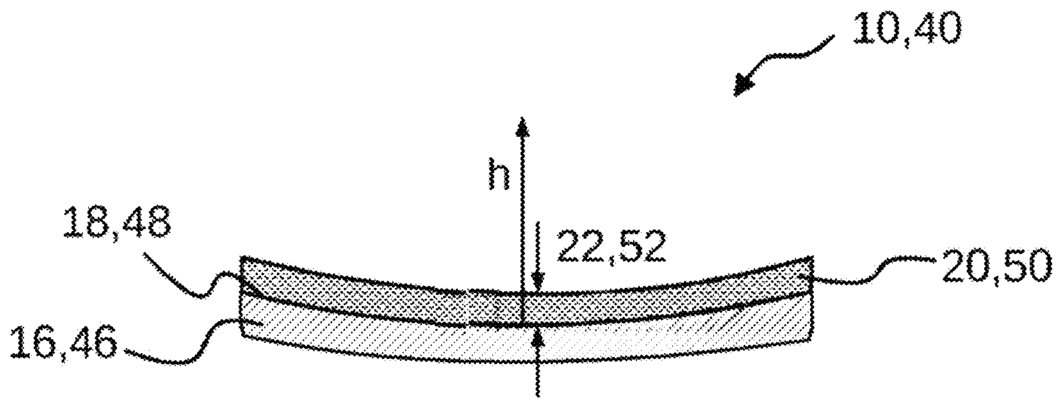
FIG. 4 is a schematic diagram illustrating a cross sectional view of the first brace part or the second brace part of the exemplary brace, FIGS. 5*a* and 5*b* schematically illustrates stress-strain relationships.

FIG. 4 is a schematic diagram illustrating a cross sectional view of the first brace part 10 or the second brace part 40 of the exemplary brace 2, as illustrated in the previous figures. The one or more first and second lattice structures 20, 50 have respective first and second heights 22, 52 in a height direction h normal to the respective inner side 18, 48 of the rigid outer shell 16,46. The illustrated example, shows the heights 22, 52 in a non-compressed state. In case of compression, i.e. a decrease in the height, the lattice structures 20, 50 are adapted to exhibit stress, which when being compressed from the non-compressed state to a first compression amount in the height direction h, increases at a first rate. When further being compressed from the first compression amount to a second compression amount, the lattice structures 20, 50 are adapted to exhibit stress being uniform or increasing at a second rate lower than the first rate.

Figure 5:
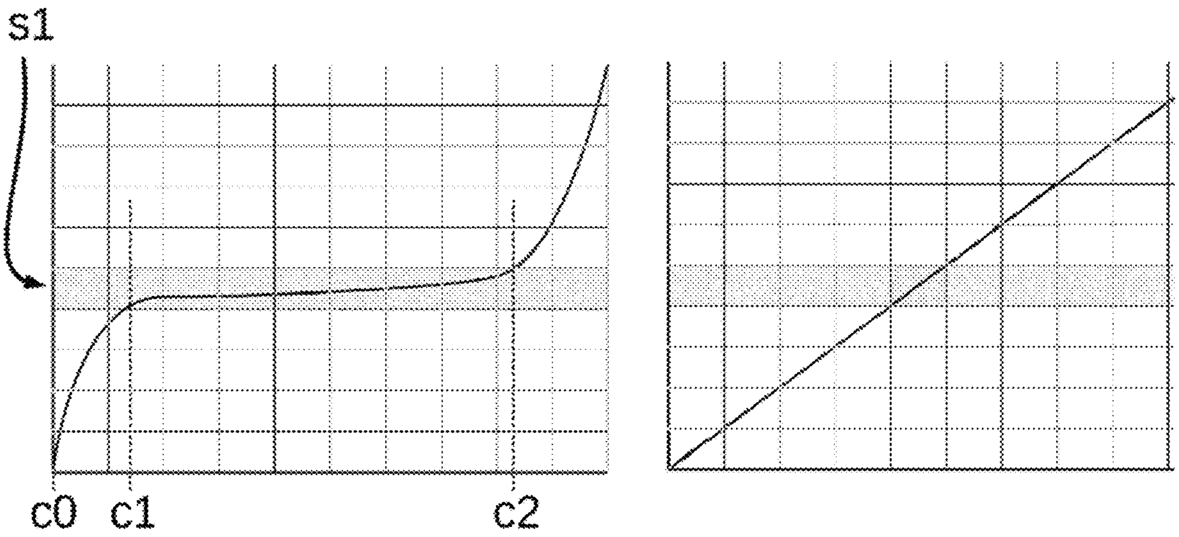

The stress strain relationship is illustrated in FIG. 5*a*, which schematically illustrates an exemplary stress-strain curve for a lattice structure, such as the one or more first and/or second lattice structures 20, 50. The horizontal axis is strain, i.e. the amount of compression, whereas the vertical axis is showing stress, i.e. pressure or force, exhibited by the lattice structure when being compressed. As mentioned, when being compressed from the non-compressed state c0 to a first compression amount c1, the lattice structures 20, 50 exhibits stress increasing at a first rate. This may be referred to as the linear elasticity zone. When further being compressed from the first compression amount c1 to a second compression amount c2, the lattice structures 20, 50 are adapted to exhibit stress being uniform or increasing at a second rate lower than the first rate. This may be referred to as a plateau zone. In response to decreasing compression from the second compression amount c2 and/or from the first compression amount c1 to the non-compressed state c1, the lattice structures 20, 50 return to their initial height 22, 52. Returning to the initial height may take some time, but is preferably a short time, i.e. seconds or milliseconds. The first compression amount c1 may correspond to 5% compression, such as less than 5% compression.

The second compression amount c2 may correspond to more than 50% compression, such as 50%. 60%, 70%, 80% or 90% compression, or more than 60%, 70%, 80% or 90% compression.

When being further compressed beyond the second compression amount c2, the lattice structures 20, 50 may exhibit stress increasing at a third rate. For the purpose of the brace as disclosed herein, it is intended that the lattice structures are compressed to between the first compression amount c1 and the second compression amount c2, when being fastened to the anatomical structure. Thereby, substantially the same pressure will be applied to the anatomical structure even if swelling is reduced or if swelling occurs after applying the brace.

FIG. 5*b* schematically illustrates, for comparison, an exemplary stress-strain curve for a regular padding of a brace.

The greyed area in the middle of the graphs in FIGS. 5*a* and 5*b*, illustrates optimal pressure or force s1 to be applied to the anatomical structure. As seen, the lattice structures 20, 50 are preferably designed such that the stress exhibited in the plateau zone, i.e. between the first compression amount c1 and the second compression amount c2, is within this optimal value s1. For comparison, as seen in FIG. 5*b*, only a very specific compression of the padding results in a stress corresponding to the optimal value, which means that, for example, a reduced swelling will result in the brace becoming loose and not sufficiently supporting the anatomical structure as intended.

Figure 6:
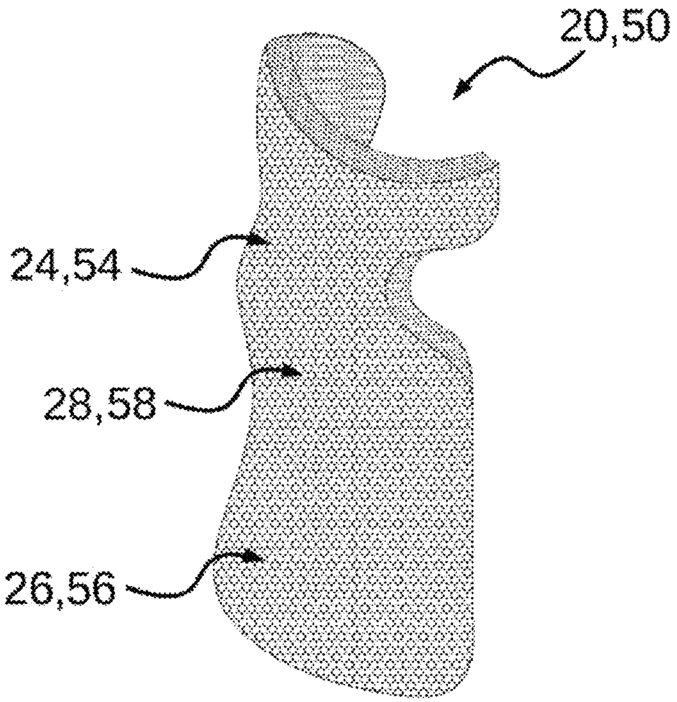
FIG. 6 is a schematic diagram illustrating an exemplary lattice structure, FIGS. 7*a*-7*c* schematically illustrates exemplary lattice structures.

FIG. 6 is a schematic diagram illustrating an exemplary lattice structure 20, 50, e.g. of the brace 2 as described with respect to the previous figures. The illustrated example shows the one or more first lattice structures 20 as also shown in FIG. 2. However, it should be understood that the one or more second lattice structures 50 of FIG. 2 may comprise the same overall features, although possibly being differently shaped. Thus, for simplicity, the present explanation with reference to FIG. 6 is provided with respect to both the one or more first lattice structures 20 and the one or more second lattice structures 50.

The one or more lattice structures 20, 50 comprises a plurality of regions including a primary region 24, 54 and a secondary region 26, 56. The plurality of regions may further comprise a tertiary region 28, 58. These regions may differ by being provided with different hardness, i.e. exhibiting different stress in the plateau zone, as explained in relation with FIG. 5. This may provide for the stabilizing of the anatomical structure being maintained mainly by parts of the anatomical structure, which may be subject to a certain amount of pressure, while relieving other parts of the anatomical structure, such as joints or bony prominences, from too much pressure. For example, the brace may be adapted to be positioned on the anatomical structure such that the primary region 24, 54, which is softer than the secondary region 26, 56 is positioned closer to the joint and/or injury of the anatomical structure than the secondary region 26, 56. For example, the primary region 24, 54 may be positioned over the joint and/or injury. The brace may be adapted to be positioned on the anatomical structure such that the (softer) primary region 24, 54 is positioned on a part of the anatomical structure having a bony prominence and/or such that the (harder) secondary region 26, 56 is positioned on a part of the anatomical structure with soft tissue, such as the forearm.

Figure 7:
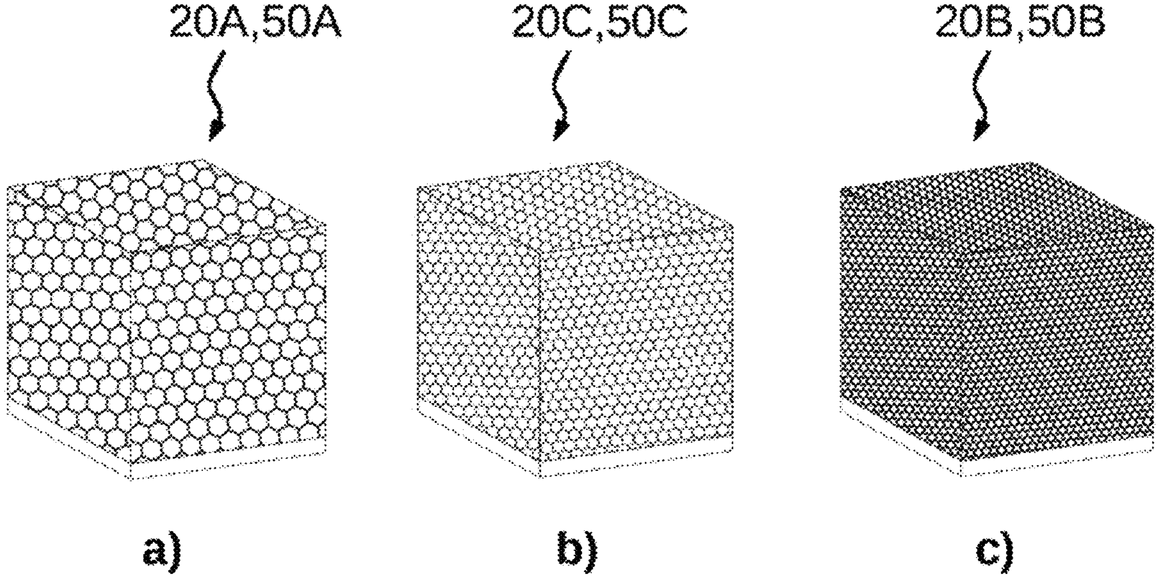

The differing hardness in the different regions is achieved by the lattice structures 20, 50 comprising different lattice structures in the different regions. Some examples, of different lattice structures are provided in FIG. 7. For example, the lattice structures 20, 50 may include a primary lattice structure 20A, 50A, as illustrated in FIG. 7*a*. The primary lattice structure 20A, 50A may cover the primary region 24, 54. The lattice structures 20, 50 may include a secondary lattice structure 20B, 50B, as illustrated in FIG. 7*c*. The secondary lattice structure 20B, 50B may cover the secondary region 26, 56. The average stress exhibited by the primary lattice structure 20A, 50A in response to compression in the plateau zone (i.e. between the first compression amount c1 and the second compression amount c2, cf. FIG. 5) is lower than the average stress exhibited by the first secondary lattice structure 20B, 50B in response to compression in the plateau zone (i.e. between the first compression amount c1 and the second compression amount c2, cf. FIG. 5). As illustrated, this difference in exhibited stress, may be achieved by changing the structure of the lattice, e.g. by changing the size of the structures of the lattice, e.g. the length of the individual struts. However, the exhibited stress may also be modified by changing the geometrical shape of the lattice, the thickness of the individual struts.

The lattice structures 20, 50 may include a tertiary lattice structure 20C, 50C, as illustrated in FIG. 7*b*. The tertiary lattice structure 20C, 50C may cover the tertiary region 28, 58. The average stress exhibited by the primary lattice structure 20A, 20A in response to compression in the plateau zone may be lower than the average stress exhibited by the tertiary lattice structure 20C, 50C in response to compression in the plateau zone. The average stress exhibited by the tertiary lattice structure 20C, 20C in response to compression in the plateau zone may be lower than the average stress exhibited by the secondary lattice structure 20B, 50B in response to compression in the plateau zone. The average stress exhibited by the tertiary lattice structure 20C, 20C in response to compression in the plateau zone may be between the average stress exhibited by the primary lattice structure 20A, 50A in response to compression in the plateau zone and the average stress exhibited by the secondary lattice structure 20B, 50B in response to compression in the plateau zone.

Although not specifically illustrated, it is noted that the lattice structures, such as their geometrical shape, thickness of struts, and/or length of struts, may vary along the height of the lattice structure, i.e. along the height direction h1 (cf. FIG. 4). Thus, the lattice structure, e.g. in one or more regions 24, 26, 28, 54, 56, 58 may have one structure, e.g. corresponding to the lattice structure as illustrated in FIG. 7*a* towards the rigid outer shell, while having another lattice structure, e.g. corresponding to the lattice structure as illustrated in FIG. 7*c* towards the anatomical structure.

Although being described collectively with reference to FIGS. 6 and 7, it should be understood that the stress-strain relationships within regions of the one or more first lattice structures 20 may differ from the stress-strain relationships within regions of the one or more second lattice structures 50.

FIG. 8 is a schematic diagram illustrating an exemplary brace 2'. The exemplary brace 2' comprises a first brace part 10, which is similar to the first brace part 10 of the brace 2 of FIG. 3. Thus, for the description of the first brace part 10, reference is made to the corresponding description in relation to FIG. 3. The brace 2' also comprises a second brace part 40', which slightly differ from the brace part 40 of the brace 2 of FIG. 3, in that the second brace part 40' is provided without the one or more lattice structures. The lattice structures may in some situations be omitted from at least one of the brace parts. Thus, in the illustrated example, the second inner side 48 of the second rigid outer shell 46 may be abutting the second part of the anatomical structure.

Although not specifically illustrated in FIG. 8, it should be understood that the brace 2', similar to the brace 2 of FIG. 3 may comprise fasteners adapted to fasten the brace 2' to the anatomical structure, e.g. by fastening the first brace part 10 to the second brace part 40'.

Figure 9:
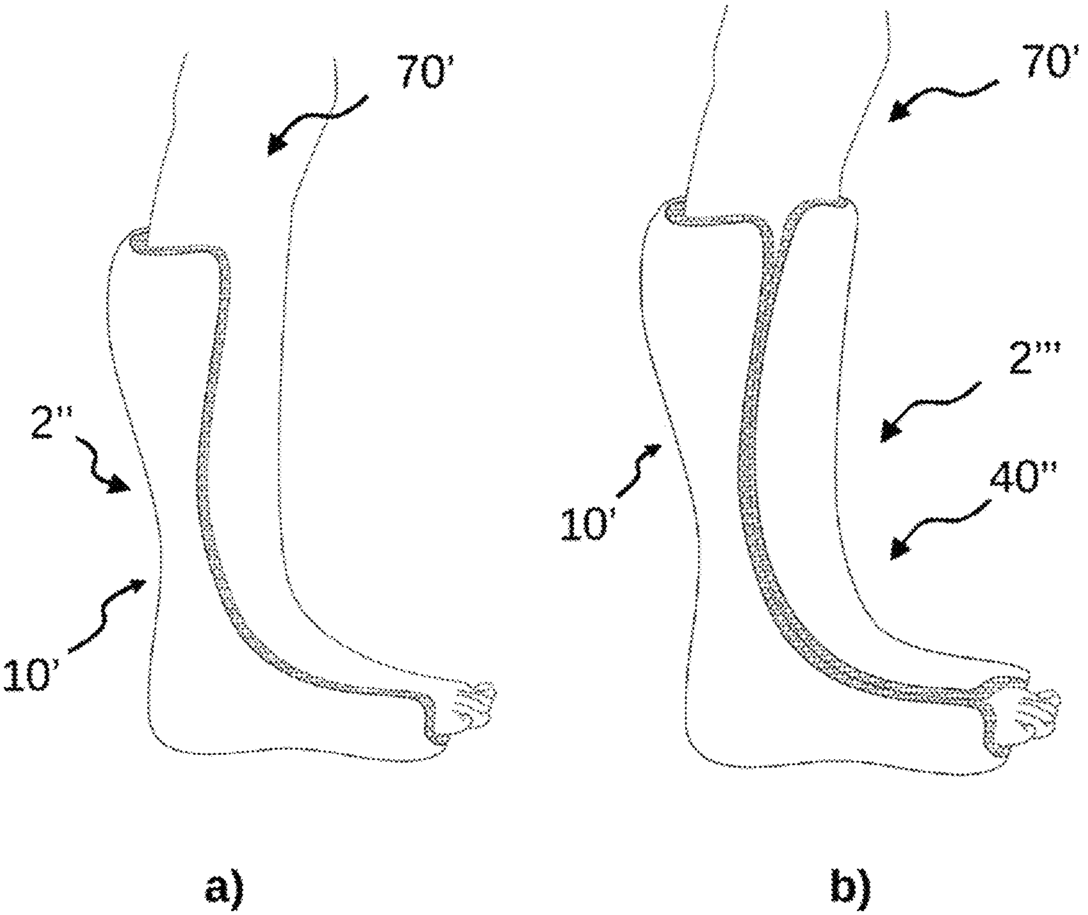
FIGS. 9*a* and 9*b* are schematic diagrams illustrating exemplary braces.

FIGS. 9*a* and 9*b* are schematic diagrams each illustrating an exemplary braces 2", 2", according to the present disclosure. More specifically FIGS. 9*a* and 9*b* are examples of braces 2", 2'" being adapted to be attached to another exemplary anatomical structure 70', wherein the anatomical structure 70' as depicted in FIGS. 9*a* and 9*b*, comprises a leg, an ankle and/or a foot. Other than being shaped differently, and the different regions of the one or more lattice structures being arranged differently to accommodate the shape and anatomy of the leg/ankle/foot, the braces 2" 2'" are similar to the braces as described previously. FIG. 9*a* show an example of a brace 2" comprising only the first brace part 10'. FIG. 9*b* shows an example of a brace 2'" comprising both the first brace part 10' and the second brace part 40".

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES

2 brace
4 fastener
10 first brace part
12 first primary brace part end
14 first secondary brace part end
16 first rigid outer shell
18 first inner side
20 first lattice structure
20A first primary lattice structure
20B first secondary lattice structure
20C first tertiary lattice structure
22 first height
24 first primary region
26 first secondary region
28 first tertiary region
40 second brace part
42 second primary brace part end
44 second secondary brace part end
46 second rigid outer shell
48 second inner side
50 second lattice structure
50A second primary lattice structure
50B second secondary lattice structure
50C second tertiary lattice structure
52 second height
54 second primary region
56 second secondary region
58 second tertiary region
70 anatomical structure
72 primary anatomical structure
74 secondary anatomical structure
76 joint
78 injury
80 first part
82 second part

The invention claimed is:

1. A brace for management of an anatomical structure comprising a primary anatomical structure, a secondary anatomical structure, and a joint and/or an injury between the primary anatomical structure and the secondary anatomical structure, the brace comprising:

a first brace part extending from a first primary brace part end to a first secondary brace part end and being configured for positioning to cover a first part of the anatomical structure extending over the joint and/or the injury such that the first primary brace part end is located on the primary anatomical structure and the first secondary brace part end is located on the secondary anatomical structure, wherein the first brace part comprises a first outer shell and one or more first lattice structures attached to a first inner side of the first outer shell, wherein the one or more first lattice structures has a first height in a height direction normal to the first inner side of the first outer shell in a non-compressed state, the one or more first lattice structures configured to:

in response to increasing compression from the non-compressed state to a first compression amount in the height direction, exhibit stress increasing at a first rate, in response to increasing compression from the first compression amount to a second compression amount in the height direction, exhibit stress being uniform or increasing at a second rate lower than the first rate, wherein the second compression amount corresponds to more than 50% of the first height, and in response to decreasing compression from the second compression amount to the non-compressed state in the height direction, return to the first height, wherein the one or more first lattice structures comprises a first primary lattice structure covering a first primary region and a first secondary lattice structure covering a first secondary region, wherein an average stress exhibited by the first primary lattice structure in response to compression between the first compression amount and the second compression amount in the first primary region is lower than an average stress exhibited by the first secondary lattice structure in response to compression between the first compression amount and the second compression amount in the first secondary region.

2. The brace of claim 1, further comprising a second brace part extending from a second primary brace part end to a second secondary brace part end and configured for positioning to cover a second part opposite the first part of the anatomical structure extending over the joint and/or the injury such that the second primary brace part end is located on the primary anatomical structure and the second secondary brace part end is located on the secondary anatomical structure, the second brace part comprising a second outer shell.

3. The brace of claim 2, wherein the second brace part comprises one or more second lattice structures attached to a second inner side of the second outer shell, the one or more second lattice structures having a second height in a height direction normal to the second inner side of the second outer shell in a non-compressed state, and the one or more second lattice structures configured to:

in response to increasing compression from the non-compressed state to a primary compression amount in the height direction, exhibit stress increasing at a primary rate, in response to increasing compression from the primary compression amount to a secondary compression amount in the height direction, exhibit stress being uniform or increasing at a secondary rate lower than the primary rate, and in response to decreasing compression from the secondary compression amount to the non-compressed state in the height direction, return to the second height.

4. The brace of claim 3, wherein the one or more second lattice structures covering a plurality of second regions including a second primary region and a second secondary region, wherein an average stress exhibited by the one or more second lattice structures in response to compression between the primary compression amount and the secondary compression amount in the second primary region is lower than an average stress exhibited by the one or more second lattice structures in response to compression between the primary compression amount and the secondary compression amount in the second secondary region.

5. The brace of claim 1, wherein the first primary lattice structure and the first secondary lattice structure are independently manufactured lattice structures.

6. The brace of claim 1, wherein the first primary lattice structure and the first secondary lattice structure are integrally formed.

7. The brace of claim 1, wherein the first primary lattice structure differs from the first secondary lattice structure.

8. The brace of claim 1, wherein the brace is configured to be positioned on the anatomical structure such that the first primary region is positioned on a part of the anatomical structure having a bony prominence and/or such that the first secondary region is positioned on a part of the anatomical structure with soft tissue.

9. The brace of claim 1, wherein the brace is configured for positioning on the anatomical structure such that the first primary region is positioned over the joint and/or injury of the anatomical structure.

10. The brace of claim 1, wherein the one or more first lattice structures comprises a first tertiary lattice structure covering a first tertiary region, wherein the average stress exhibited by the first primary lattice structure in response to compression between the first compression amount and the second compression amount in the first primary region is lower than an average stress exhibited by the first tertiary lattice structure in response to compression between the first compression amount and the second compression amount in the first tertiary region.

11. The brace of claim 1, further comprising one or more fasteners configured to fasten the brace to the anatomical structure, the one or more fasteners comprises one or more straps.

12. A method for manufacturing a brace for management of an anatomical structure comprising a primary anatomical structure, a secondary anatomical structure, and a joint and/or an injury between the primary anatomical structure and the secondary anatomical structure, the method comprising:

providing a first outer shell for a first brace part of the brace extending from a first primary brace part end to a first secondary brace part end, wherein the first brace part is configured for positioning to cover a first part of the anatomical structure extending over the joint and/or injury such that the first primary brace part end is located on the primary anatomical structure and the first secondary brace part end is located on the secondary anatomical structure, forming one or more first lattice structures having a first height in a height direction in a non-compressed state, and the one or more first lattice structures being adapted to:

in response to increasing compression from the non-compressed state to a first compression amount in the height direction, exhibit stress increasing at a first rate, in response to increasing compression from the first compression amount to a second compression amount in the height direction, wherein the second compression amount corresponds to more than 50% of the first height, exhibit stress being uniform or increasing at a second rate lower than the first rate, and in response to decreasing compression from the second compression amount to the non-compressed state in the height direction, return to the first height, wherein the one or more first lattice structures are formed to include a first primary lattice structure covering a first primary region and a first secondary lattice structure covering a first secondary region, wherein an average stress exhibited by the first primary lattice structure in response to compression between the first compression amount and the second compression amount in the first primary region is lower than an average stress exhibited by the first secondary lattice structure in response to compression between the first compression amount and the second compression amount in the first secondary region, and attaching the one or more first lattice structures to a first inner side of the first outer shell, such that the height direction of the one or more first lattice structures are arranged normal to the first inner side of the first outer shell.

13. The method of claim 12, further comprising obtaining a three-dimensional model of the anatomical structure including the location of the joint and/or the injury, and wherein forming the one or more first lattice structures is based on the three-dimensional model, wherein the three-dimensional model comprises information of tissue type at a plurality of locations of the anatomical structure, and wherein forming the one or more first lattice structures and/or attaching the one or more first lattice structures to the first inner side of the first outer shell comprises arranging the first primary region to cover a part of the anatomical structure having bony prominences and the first secondary region to cover a part of the anatomical structure having soft tissue.

14. The method of claim 12, wherein forming the one or more first lattice structures comprises forming a single lattice structure comprising the first primary lattice structure and the first secondary lattice structure and/or being configured to extend from the first primary brace part end to the first secondary brace part end.

* * * * *